(12) United States Patent
Kreiβ et al.

(10) Patent No.: US 7,333,195 B2
(45) Date of Patent: Feb. 19, 2008

(54) METHOD FOR DETECTING PHOTOSYNTHESIS INHIBITION

(75) Inventors: Wolfgang Kreiβ, Bergisch Gladbach (DE); Mark Wilhelm Drewes, Langenfeld (DE); Günther Eberz, Odenthal-Holz (DE); Norbert Caspers, Kürten-Bechen (DE)

(73) Assignee: Bayer Innovation GmbH, Dusseldorf (DE)

( * ) Notice: Subject to any disclaimer, the term of this patent is extended or adjusted under 35 U.S.C. 154(b) by 361 days.

(21) Appl. No.: 10/482,990

(22) PCT Filed: Jun. 26, 2002

(86) PCT No.: PCT/EP02/07057

§ 371 (c)(1),
(2), (4) Date: Jan. 7, 2004

(87) PCT Pub. No.: WO03/006684

PCT Pub. Date: Jan. 23, 2003

(65) Prior Publication Data

US 2004/0178358 A1    Sep. 16, 2004

(30) Foreign Application Priority Data

Jul. 9, 2001 (DE) ............................... 101 33 273

(51) Int. Cl.
*G01J 3/30* (2006.01)

(52) U.S. Cl. .................. 356/317; 356/318; 250/459.1; 250/461.2

(58) Field of Classification Search ................ 356/317, 356/318, 288; 800/290, 288; 435/172, 418, 435/288.7; 250/459.1, 461.2, 462.1
See application file for complete search history.

(56) References Cited

U.S. PATENT DOCUMENTS 6,238,928 B1    5/2001   Weisemann et al. ........ 436/162
6,483,582 B2 *  11/2002  Modlin et al. .............. 356/317

FOREIGN PATENT DOCUMENTS

| CA | 2303529  | 10/2000 |
| EP | 1 134 585 | 9/2001 |
| WO | 99/19900 | 4/1999 |

OTHER PUBLICATIONS

Koblizek et al , A Sensitive Photosystem II-Based Biosensor for Detection of a Class of Herbicides, Dec. 1998, Biotechnology and Bioengineering, vol. 60, No. 6.*

Herbizide [Herbicides], Georg Thieme Verlag, (month unavailable) 1954, pp. 54 and 112-114, B. Hock, C. Fedtke, R.R. Schmidt, p. 54, "Labortesst und Gewächshausscreening", p. 112-114 "Methoden und Meβparameter zur Messung von Photosyntheseleistungen".

Fresenius J. Anal. Chem., 354, (month unavailable) 1996, pp. 299-305, Daniela Merz, Michael Geyer, David A. Moss, Hans-Joachim Ache, "Chlorophyll fluorescence biosensor for the detection of herbicides".

Methoden der biologischen Wasseruntersuchung [Method of Biological Water Analytics], vol. 2, Biologische Gewässeruntersuchung, G. Fisher Verlag (month unavailable) 1999, pp. 386-388 "Verfahren und Geräte zur Messung der verzögerten Fluoreszenze (DF)".

Oecologia, 102, (month unavailable) 1995, pp. 425-432, Wolfgang Bilger, Ulrich Schreiber, Michael Bock, "Determination of the quantum efficiency of photosystem II and of non-photochemical quenching of chlorophyll fluorescence in the field".

Koblizek Michal et al: A biosensor for the detection of triazine and phenylurea herbicides designed using photosystem II coupled to a screen-printed electrode.: Biotechnology and Bioengineering, vol. 78, No. 1, Apr. 5, 2002, pp. 110-116, XP002219048.

Brewster JD et al.: "Storage and immobilization of Photosystem II reaction centers used in an assay for herbicides" Anal Chem, vol. 67, 1995, pp. 1296-1299, XP002219049.

Kapur R et al: "Streamlinging the drug discovery process by integrating miniaturization, high content screening, and automation on the CellChip/sup TM/ system" Biomedical Microdevices, 1999, Kluwer Academic Publishers, USA, vol. 2, No. 2, pp. 99-109, XP002162337.

Hideaki Matsuoka et al: "CO2 Stress Sensing Using a Tobacco Leaf on the Basis of Chlorophyll-fluorescence Analysis" Sensors and Actuators B, Elsevier Sequoia S.A., Lausanne, CH, vol. B 17, No. 2, 1994, pp. 85-92, XP000428653.

\* cited by examiner

*Primary Examiner*—Layla G. Lauchman
(74) *Attorney, Agent, or Firm*—Womble Carlyle Sandridge & Rice

(57) ABSTRACT

This invention relates to a method for detecting the photosynthesis-inhibitory activity of substances by providing cells or cell parts with an intact photosystem, introducing the cells or cell parts into a planar layer, applying the test substance to the planar layer or into the planar layer, excitation of the luminescence of the cells or cell parts in the planar layer by an excitation light source, measuring the luminescence of the cells or the cell parts in the planar layer by means of a detector, and associating the detector signal with the degree of photosynthesis inhibition.

17 Claims, 2 Drawing Sheets

METHOD FOR DETECTING PHOTOSYNTHESIS INHIBITION

RELATED APPLICATIONS

The present patent application has been filed under 35 U.S.C. 371 as a national stage application of PCT/EP02/07057, filed Jun. 26, 2002, which was published in German as International Patent Publication WO 03/006684 on Jan. 23, 2003, which is entitled to the right of priority of German Patent Application 101 33 273.4, filed Jul. 9, 2001.

BACKGROUND OF THE INVENTION

A variety of tests, both on higher plants and on microalgae, are known for assaying photosynthesis-inhibitory activity. The known measuring principles are based, inter alia, on the fluorescence of chlorophyll or on measuring the photosynthetic oxygen production (B. Hock, C. Fedtke, R. R. Schmidt, Herbizide [Herbicides], Georg Thieme Verlag, 1995, 54 and 112-114; D. Merz, M. Geyer, D. A. Moss, H.-J. Ache, Fresenius J. Anal. Chem, 1996, 354: 299-305). All of these methods, which represent the prior art, have limitations which do not permit high-throughput measurements as they are carried out in the screening of active ingredients, miniaturization, for example a high degree of parallerlization, or a direct couplings with analytical separation techniques for detecting activities in substance mixtures.

Measuring the fluorescence of chlorophyll is an established standard method for studying the photosynthesis process. The methods used in this context rely on fluorimeters which, owing to their methodology, which is based on measurements using probes or cuvettes, only permit serial measurements and are therefore not suitable for high-throughput applications. Moreover, such methods are also very difficult to miniaturize. Typical instruments for this technique are available from the manufacturers mentioned hereinbelow, among others: ADO BioScientific Ltd., Hansatech Instruments, Heinz Walz GmBH, Qubit Systems Inc.

In the DF-Algentest [DF algae test], water samples are treated with green algae and subsequently measured luminometrically (Methoden der biologischen Wasser-untersuchung [Methods of Biological Water Analytics], Volume 2: Biologische Gewässeruntersuchung, G. Fischer Verlag, 1999, page 386-388). In this test, the first step is the determination of deactivation kinetics for the lagging luminescence of the photosynthesis pigment complex. Conclusions regarding the presence of photosynthesis-inhibitory substances are drawn by comparison with the corresponding deactivation kinetics for an untreated reference sample. This method is only capable of processing samples in series and is thus not suitable for high-throughput measurements.

A further limitation relates to the sample volume for the DF-Algentest, which, owing to the dimensions of the equipment, is in the milliliter order. This method does not allow miniaturization. Moreover, substance mixtures, as are typical for realistic samples, can only be assessed in their entirety by this method. Owing to the possibility of interactions between the sample constituents, there is a risk of false positives.

Tests on higher plants are also known (see, for example, W. Bilger, U. Schreiber, M. Bock, Oecologia 102, 1995, pp. 425-432). These tests provide findings on photosynthetic inhibition via a method in which the fluorescence is measured. Again, the geometry of the test device prevents a high degree of parallerlization and miniaturization. Again, substance mixtures can only be assessed in their entirety.

EP 588 139 A1 describes a test for substance mixtures. The biological effect of the substances in a substance mixture is tested by a combination of chromatographic separation of the substance mixture into the substances to be tested in chromatographic zones, followed by a bioassay (toxicity) of the individual fractions which have been separated. In the bioassay, the individual fractions are brought into contact with luminescence microorganisms which indicate the biological effect of this fraction by means of a local change in their bioluminescence at the individual fractions.

The possibility of parallerlization and miniaturization of activity assays is described in EP 1 043 582 A2. According to the method disclosed in EP 1 043 582 A2, a sensor layer consisting of a diffusion-controlling matrix in which activity sensors are suspended is employed. The bioactivity of the test substances is indicated by optical signals upon contact of this sensor layer with samples.

The object of the invention consists in providing a device and a method for detecting photosynthesis-inhibitory substances which makes possible miniaturization and a markedly higher sample throughput in comparison with the prior art.

The object of the invention is achieved by a method for detecting the photosynthesis-inhibitory activity of substances, comprising the following steps:
  providing cells or cell parts with an intact photosystem,
  introducing the cells or cell parts into a planar layer,
  applying the test substance to the planar layer or into the planar layer,
  exciting the luminescence of the cells or cell parts in the planar layer by an excitation light source,
  measuring the luminescence of the cells or cell parts in the planar layer by means of a detector, and
  associating the detector signal with the degree of photosynthesis inhibition.

DETAILED DESCRIPTION OF THE INVENTION

Figure 1:
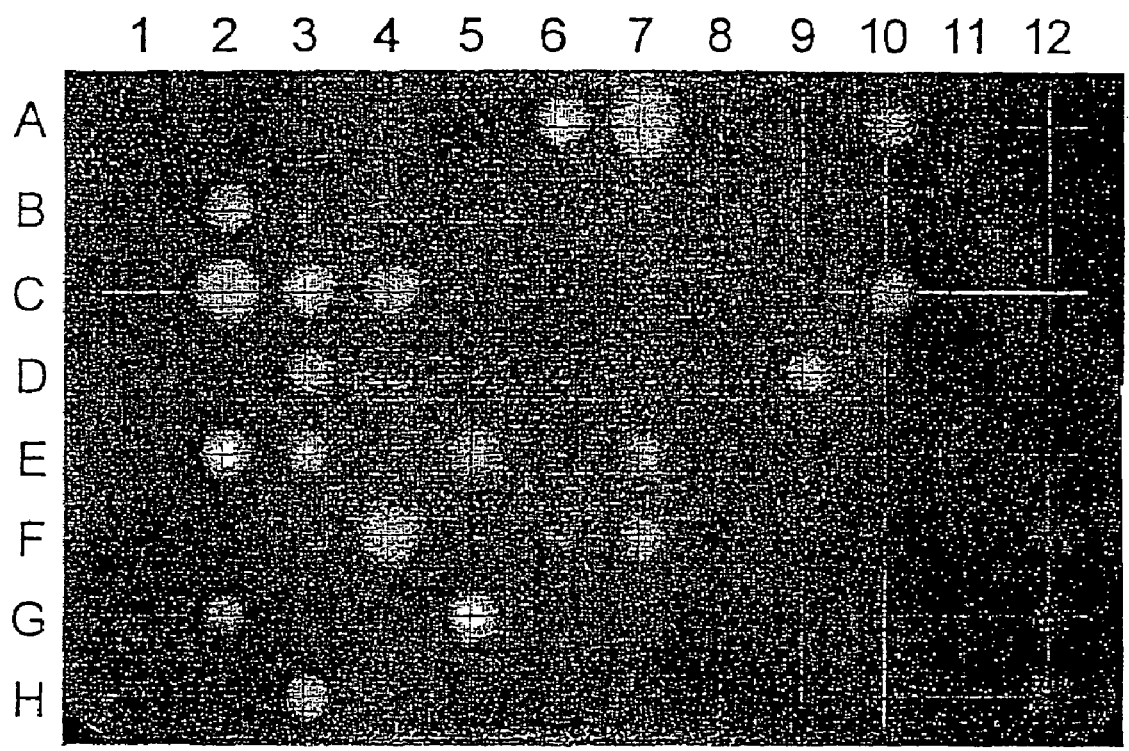
FIGS. 1 and 2 are fluorescent images obtained according to Examples 1 and 2, respectively.

The cells may be derived from algae, microalgae, bacteria, in particular cyanobacteria, which has a photosynthesis system, plant cell cultures or plant homogenate. The method also operates with cells whose vitality is damaged, as long as an intact photosystem II (PS II) is present.

The cells may also originate from selected mutants or from genetically modified organisms.

The planar layer is preferably a gel layer. The planar layer preferably has a thickness in the range of from 0.1 mm to 10 mm. The cells or cell parts can be introduced into a planar layer by embedding for example green algae in agarose or acrylate gels or other gellants or viscous media.

Application of the test substance to the planar layer or into the planar layer is effected for example by syringe techniques or pin tools or suitable pressure techniques (jet systems and the like), preferably in the form of spots.

The luminescence is fluorescence and/or phosphorescence (lagged luminescence). Measuring the phosphorescence is advantageous over measuring the fluorescence since there is no need to discriminate between excitation and emission. On the other hand, measurement with fluorescence is advantageous owing to its higher sensitivity.

Suitable excitation light sources are not only white-light sources, for example halogen light or fluorescent tubes, but also light sources which emit within a narrow spectral range, for example light-emitting diodes. Daylight may also act as the excitation light source. Excitation may be continuous or in a pulsed mode (pulse modulation technique).

Detection is effected with instruments which are capable of imaging the emitted luminescence in a wavelength range of >680 nm with sufficient sensitivity (for example Vidicon System, CCD camera, scanner, phosphorimager, photographic film).

Time-resolved light measurements, if appropriate together with pulsed excitation and correlation of excitation and measurement, may also be carried out.

Independently of excitation exposure, supplementary illumination or a dark phase for controlling the photosynthesis activity may be employed.

Photosynthesis-inhibitory test substances which are applied to or onto the planar layer according to the invention affect the luminescent behavior of the photosynthesis pigment complex. Spots of photosynthesis inhibitors, such as atrazine, which are applied to the planar layer can be detected simply, and in the case of a large number of spots, simultaneously via their activity, for example by a significant weakening of the lagged luminescence (phosphorescence), using videoimaging methods. As an alternative, the increased fluorescence of the photo-pigments when the photosystem II is inhibited may also be used for imaging the PS II-active substance spots.

The invention furthermore relates to a system for detecting the photosynthesis-inhibitory activity of substances by the method according to the invention, comprising
  a planar layer with cells or cell parts with an intact photosystem,
  means for applying the test substance to the planar layer or into the planar layer,
  excitation light source for exciting the luminescence of the cells or the cell parts in the planar layer,
  detector for measuring the luminescence of the cells or cell parts in the planar layer,
  evaluation means for associating the detector signal with the degree of photosynthesis inhibition.

The means for applying the test substance to the planar layer or into the planar layer can be, for example syringe systems, steel needles (pin tools) or suitable pressure stamps, and also jet systems.

The evaluation can be effected visually or by means of suitable imaging techniques.

The invention furthermore relates to a test strip or sensor chip for detecting the photosynthesis-inhibitory activity of substances by the method according to the invention comprising a planar layer with cells or cell parts with an intact photosystem, where, after the test substance has been applied to the planar layer or into the planar layer, and after the subsequent excitation of the luminescence of the cells or the cell parts in the planar layer by an excitation light source, and after measuring the luminescence of the cells or the cell parts in the planar layer with a detector, the degree of photosynthesis inhibition can be determined on the basis of the detector signal.

The planar layer of the test strip or sensor chip consists preferably of green algae in agarose or acrylate gels. In this manner, stable detection layers can be prepared which retain their function as test system for a photosynthesis-inhibitory activity even when stored over prolonged periods.

An advantage of the method according to the invention is the high degree of miniaturization and parallerlization of the detection method for photosynthesis-inhibitory substances. Parallerlization allows a high sample throughput to be achieved. Miniaturization allows one to make do with considerably less material.

The method according to the invention makes it possible to apply several thousands of substance spots to an area of 9 cm *12 cm and thus to achieve not only parallerlization, but a degree of miniaturization of <10 ng of test substance in less than 500 nl of test volume.

The space-resolving analysis permits the identification of photosynthesis-inhibitory substances as components of substance mixtures in thin-layer chromatograms or electropherograms in a trouble-free manner by first subjecting the substance mixture to chromatographic or electrophoretic separation on a thin-layer chromatography plate or an electrophoresis layer and subsequently studying the photosynthesis-inhibitory activity of the fractions by the method according to the invention. This invention relates to a method for detecting the photosynthesis-inhibitory activity of substances by providing cells or cell parts with an intact photosystem, introducing the cells or cell parts into a planar layer, applying the test substance to the planar layer or into the planar layer, excitation of the luminescence of the cells or cell parts in the planar layer by an excitation light source, measuring the luminescence of the cells or the cell parts in the planar layer by means of a detector, and associating the detector signal with the degree of photosynthesis inhibition.

The space-resolving analysis also permits the application of photosynthesis-inhibitory substances to different positions of a support and to study the photosynthesis-inhibitory activity of these spots by the method according to the invention.

The method according to the invention can be employed in active ingredient research for the optimization of photosynthesis inhibitors. A further field of application is, for example, the specific measurement of the herbicidal activity in wastewater and environmental samples which can be attributed to pollutants.

EXAMPLE 1

Example 1 shows the specific detection by the method according to the invention of photosynthesis-inhibitory substances by means of induced fluorescence in the layer system according to the invention.

A thin agarose layer (layer thickness approx. 4 mm) in which green algae (*Scenedesmus subspicatus*) had been suspended, was employed to detect the photosynthesis-inhibitory action.

The green algae were grown as follows:

The algae from a *Scenedesmus subspicatus* stock are used to inoculate 50 ml of growth medium in a sterile 100 ml Erlenmeyer flask. The solution is subsequently incubated for 7 days at 23° C. and 125 rpm in a controlled-environment cabinet equipped with fluorescent tubes, with exposure to light.

The growth medium contains:

58 mg/l sodium carbonate 496 mg/l sodium nitrate 39 mg/l potassium hydrogenphosphate 75 mg/l magnesium sulfate heptahydrate 36 mg/l calcium chloride dihydrate 10 mg/l Titriplex III 3 mg/l citric acid and is brought to pH 7.5±0.2 using 1 N HCl and/or 1 N NaOH. Prior to use, the medium is autoclaved for 20 minutes at 121° C.

Preparation of the Algal Layer:

25 ml of the algal suspension (optical density approx. 2 mAU) are mixed at temperatures of below 40° C. with 15 ml of 1% strength agarose MP solution (Boehringer Mannheim GmbH Art. No. 1388983) until homogeneous. Before this suspension is cold, it is placed into a single-well plate (Nalge Nunc, Omni Tray Single Well 86×128 mm), where a gel layer with uniformly suspended algae is formed upon cooling. This detection layer can be employed immediately or else after several weeks' storage for measuring the photosynthesis-inhibitory action.

Substance Transfer to the Detection Layer, and Incubation:

To carry out the parallel activity test according to the invention, the algal layer is stamped with test substances from a microtiter plate, using a 96-fold pin tool (Nalge Nunc 96 Pin Replicator). The sample deposit on the microtiter plate (see Table 1) thus also lays down the position of the substance in question on the algal layer. The test substances were present in the microtiter plate in the form of a DMSO solution (100 μmol substance in 100 μl per well). Using the pin tool, in each case approx. 0.5 μl of sample solution were transferred to the detection layer per pin. Prior to the fluorescence measurement the stamped detection layer was incubated for 15 minutes at room temperature.

TABLE 1

Parallel detection of the activity of substances by fluorescence imaging on a 96-well microtiter plate with algal layer

| Position | Substance | Activity |
|---|---|---|
| A1 | — | |
| B1 | Glyphosate | |
| C1 | Thidiazuron | |
| D1 | Pendimethalin | |
| E1 | Fluazifop-P-butyl | |
| F1 | Thifensulfuron-methyl | |
| G1 | Quinmerac | |
| H1 | Ioxynil | |
| A2 | MCPA | |
| B2 | Tebuthiuron | X |
| C2 | Diuron | X |
| D2 | Mefenacet | |
| E2 | Cyanazine | X |
| F2 | Oxadiazon | |
| G2 | Terbuthylazine | X |
| H2 | Diflufenican | |
| A3 | Dicamba | |
| B3 | Acifluorfen | |
| C3 | Ametryne | X |
| D3 | Prometon | X |
| E3 | Prometryne | X |
| F3 | Sulfometuron-methyl | |
| G3 | — | |
| H3 | Metribuzin | X |
| A4 | Pyrazolate | |
| B4 | Norflurazon | |
| C4 | Linuron | X |
| D4 | EPTC | |
| E4 | Metazachlor | |
| F4 | Metamitron | X |
| G4 | Naproamid | |
| H4 | Bentazone | |
| A5 | Pyridate | |
| B5 | — | |
| C5 | Pretilachlor | |
| D5 | Sethoxydim | |
| E5 | Isoproturon | X |
| F5 | Nicosulfuron | |
| G5 | Bromacil | X |
| H5 | Haloxyfop-P-methyl | |

TABLE 1-continued

Parallel detection of the activity of substances by fluorescence imaging on a 96-well microtiter plate with algal layer

| Position | Substance | Activity |
|---|---|---|
| A6 | Phenmedipham | X |
| B6 | Alachlor | |
| C6 | — | |
| D6 | Thiobencarb | |
| E6 | Difenzoquat | |
| F6 | Imazapyr | |
| G6 | Metsulfuron-methyl | |
| H6 | Metolachlor | |
| A7 | Propanil | X |
| B7 | Clopyralid | |
| C7 | Bensulfuron-methyl | |
| D7 | — | |
| E7 | Atrazine | X |
| F7 | Simazine | X |
| G7 | — | |
| H7 | Propyzamid | |
| A8 | Quinchlorac | |
| B8 | Diquat | |
| C8 | Bifenox | |
| D8 | Glufosinate | |
| E8 | Butylate | |
| F8 | Ethalfluralin | |
| G8 | Sulcotrione | |
| H8 | Tralkoxydim | |
| A9 | Amitrole | |
| B9 | — | |
| C9 | Butachlor | |
| D9 | Hexazinon | X |
| E9 | Alloxydim | |
| F9 | Chlorimuron-ethyl | |
| G9 | — | |
| H9 | Mecoprop | |
| A10 | Fluometuron | X |
| B10 | Fenoxaprop-P-ethyl | |
| C10 | Desmedipham | X |
| D10 | Primisulfuron | |
| E10 | Di-allate | |
| F10 | Asulam | |
| G10 | — | |
| H10 | Ethofumesate | |
| F12 | 50 ng Metamitron | Reference for PSII inhibition |
| G12 | 125 ng Metamitron | Reference for PSII inhibition |
| H12 | 250 ng Metamitron | Reference for PSII inhibition |

Parallel Detection of the Activity by Fluorescent Imaging:

A videoimaging system (Molecular Light Imager Night-OWL by PerkinElmer Life Sciences) was employed for recording the fluorescence image. To carry out the measurement, the single-well plate was placed on a light table whose white-light source was limited to wavelengths of below 475 nm using a filter (Omega 475 RDF 40). For the selective detection of the fluorescence light, the camera lens was equipped with a filter which allows light above 680 nm to pass through (Andover PIN: 680FS10-50). Fluorescence excitation and recording by the camera were carried out simultaneously over a period of 1 second. The fluorescent image was evaluated visually on the screen of the videoimaging system. For documentation purposes, TIFF files were formatted with suitable graphics programs and labeled (Adobe Photoshop 5.0, MS Powerpoint 97).

Results:

The fluorescent image revealed 22 light spots (see FIG. 1). The substances deposited at these spots bring about an increased fluorescence owing to their interaction with the photosystem. Metamitron, a known photosynthesis inhibitor, has been applied as reference substance to positions F12,G12 and H12 in amounts of 50 ng, 125 ng and 250 ng. All of the substances which were noted in this parallel assay and the substances marked X in Table 1 are known inhibitors of the photosystem II.

EXAMPLE 2

Example 2 shows the specific detection by the method according to the invention of photosynthesis-inhibitory substances by means of phosphorescence in the layer system according to the invention.

The algal layer was prepared analogously to Example 1.

The same test substances as in Example were applied to the algal layer in identical positions. Incubation was likewise for 15 minutes.

Parallel Detection of the Activity by Phosphorescent Imaging:

A videoimaging system (Molecular Light Imager Night-OWL by PerkinElmer Life Sciences) was employed for recording the phosphorescence image. For the measurement, the NUNC plate was placed on a light table which was equipped with a white light source. To record the phosphorescent light, no filters were inserted before the camera lens. The algal layer was exposed for 90 seconds in order to excite phosphorescence. After a period of 15 seconds, the image was taken by the camera with an exposure time of 30 seconds. The phosphorescent image was evaluated visually on the screen of the videoimaging system. For documentation purposes, TIFF files were formatted with suitable graphics programs and labeled (Adobe Photoshop 5.0, MS Powerpoint 97).

Figure 2:
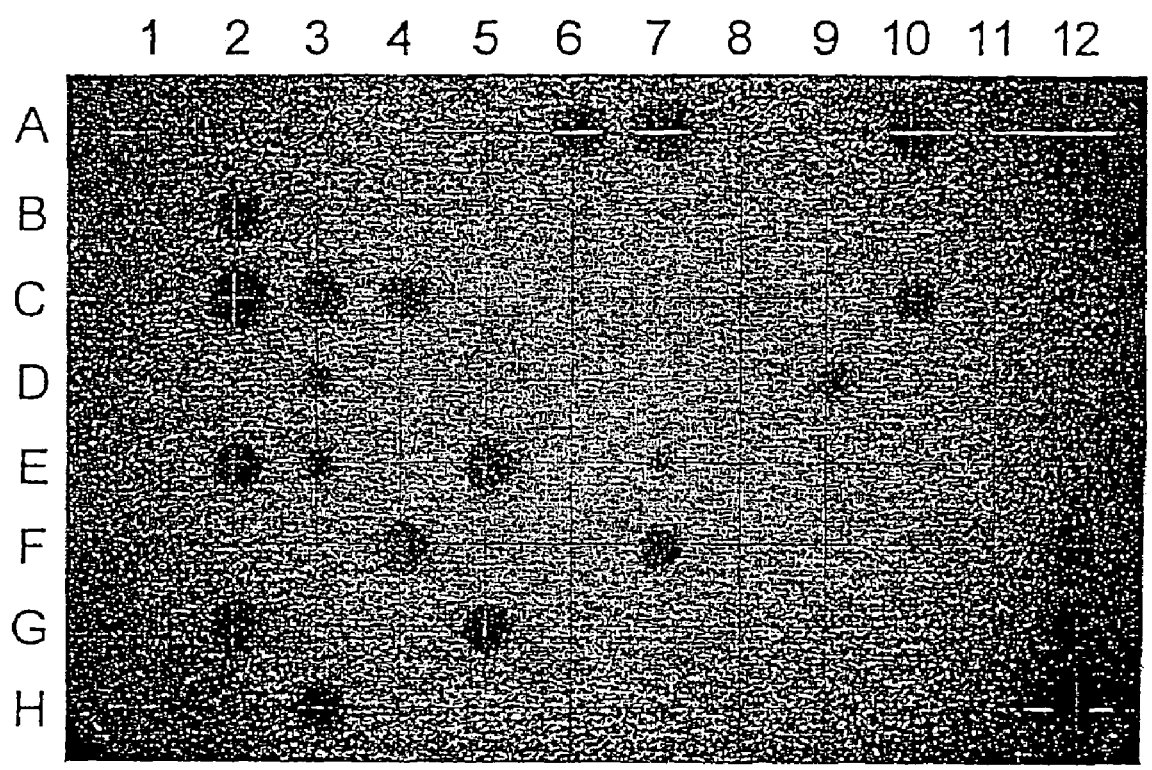

Results:

The phosphorescent image revealed 22 dark spots (see FIG. 2). The substances deposited at these spots bring about more rapid deactivation of the phosphorescence owing to their interaction with the photosystem. Metamitron, a known photosynthesis inhibitor, has been applied as reference substance to positions F12,G12 and H12 in amounts of 50 ng, 125 ng and 250 ng. The results are in good agreement with the results of the fluorescent imaging (see also Example 1). All of the substances which were noted in this parallel assay are known photosystem II inhibitors.

What is claimed is:

1. A method of detecting photosynthesis inhibitory activity of a substance comprising
   (a) providing cells or cell parts having an intact photosystem along with a planar layer,
   (b) applying a test substance to the provided cells and planar layer,
   (c) exciting luminescence of the cells or cell parts that have been contacted by the test substance by an excitation light source,
   (d) measuring an excitation value corresponding to the luminescence of the cells or cell parts by means of a detector, and
   (e) referencing the measured value against a predetermined value to determine inhibitory activity of the substance.

2. A method according to claim 1 wherein the cells are cells of algae, microalgae, cyanobacteria or other bacteria having a photosynthetic photosynthesis system, plant cell cultures or plant homogenate, selected mutants, or genetically modified organisms.

3. A method according to claim 1 wherein the cells are avital cells in which photosynthesis system II remains intact.

4. A method according to claim 1 wherein the planar layer is a gel or other viscous medium.

5. A method according to claim 4 wherein the gel is an agarose or acrylate gel.

6. A method according to claim 1 wherein the planar layer has a thickness in the range of from 0.1 mm to 10 mm.

7. A method according to claim 1 wherein the cells or the cell parts are introduced into the planar layer by embedding green algae in agarose.

8. A method according to claim 1 wherein the test substance is applied in the form of spots to the planar layer or into the planar layer by a pin tool, syringe system, or pressure technique.

9. A method according to claim 1 wherein the luminescence takes the form of fluorescence and/or phosphorescence.

10. A method according to claim 1 wherein the excitation light source is a white-light source or a light source having a narrow spectral distribution and emits light by continuous excitation and/or pulse modulation.

11. A method according to claim 10 wherein the excitation light source is daylight.

12. A method according to claim 1 wherein the luminescence is measured as an image at a wavelength range of >680 nm.

13. A method according to claim 1 wherein the luminescence is measured with a Vidicon system, a CCD camera, a scanner, a phosphorimager, or a photographic film.

14. A method according to claim 1 wherein the luminescence is measured by time-resolved light measurements, in conjunction with pulsed excitation and correlation of excitation and measurement.

15. A method of detecting photosynthesis-inhibitory activity of a substance comprising
   (a) providing cells or cell parts having an intact photosystem along with a planar layer,
   (b) providing a thin-layer chromatography plate, an electrophoresis layer, or other support with one or more zones of a substance deposited thereon,
   (c) applying the planar layer to the thin-layer chromatography plate, electrophoresis layer, or other support,
   (d) exciting luminescence of the cells or cell parts that have been contacted by the test substance by an excitation light source,
   (e) measuring an excitation value corresponding to the luminescence of the cells or cell parts by means of a detector, and
   (f) referencing the measured value against a predetermined value to determine inhibitory activity of the substance.

16. A method according to claim 15 wherein the zones of the substance have been generated by chromatographic or electrophoretic separation.

17. A method according to claim 1 wherein the luminescence is measured by time-resolved light measurements.

* * * * *